United States Patent [19]

Jackson et al.

[11] 4,232,373
[45] Nov. 4, 1980

[54] COMPENSATION OF FLUIDIC TRANSDUCERS

[75] Inventors: Leland B. Jackson; Dov Jaron, both of Kingston, R.I.

[73] Assignee: Regents for Education of the State of Rhode Island, Providence, R.I.

[21] Appl. No.: 896,357

[22] Filed: Apr. 14, 1978

[51] Int. Cl.² .................................................. G06F 7/38
[52] U.S. Cl. .................................... 364/572; 364/413; 364/724
[58] Field of Search ............... 364/571, 572, 413, 558, 364/724, 574

[56] References Cited

U.S. PATENT DOCUMENTS

| | | | |
|---|---|---|---|
| 3,275,980 | 9/1966 | Foster | 364/572 X |
| 3,287,695 | 11/1966 | Taylor | 364/572 X |
| 3,295,099 | 12/1966 | Lawrence et al. | 364/572 X |
| 3,798,432 | 3/1972 | Dobson et al. | 364/509 |
| 3,798,560 | 3/1974 | Taylor | 364/724 X |
| 3,889,108 | 6/1975 | Cantrell | 364/724 |
| 3,908,116 | 9/1975 | Bjornsen | 364/572 X |
| 3,988,606 | 10/1976 | Eggermont | 364/724 |
| 3,994,285 | 11/1976 | Doll | 364/572 X |
| 3,996,926 | 12/1976 | Birnbaum | 364/487 X |
| 4,063,082 | 12/1977 | Nussbaumer | 364/724 X |
| 4,084,248 | 4/1978 | Scott | 364/571 |

Primary Examiner—Edward J. Wise
Attorney, Agent, or Firm—Richard J. Birch

[57] ABSTRACT

The output indications of fluid-filled transducers are compensated by filtering under the control of error analyser signals. In particular, the pressure waveform of a fluid-filled catheter is sampled and used to produce error signals that control a digital filter for the samples in order to compensate for measurement errors that are attributable to the physical characteristics of the catheter.

8 Claims, 7 Drawing Figures

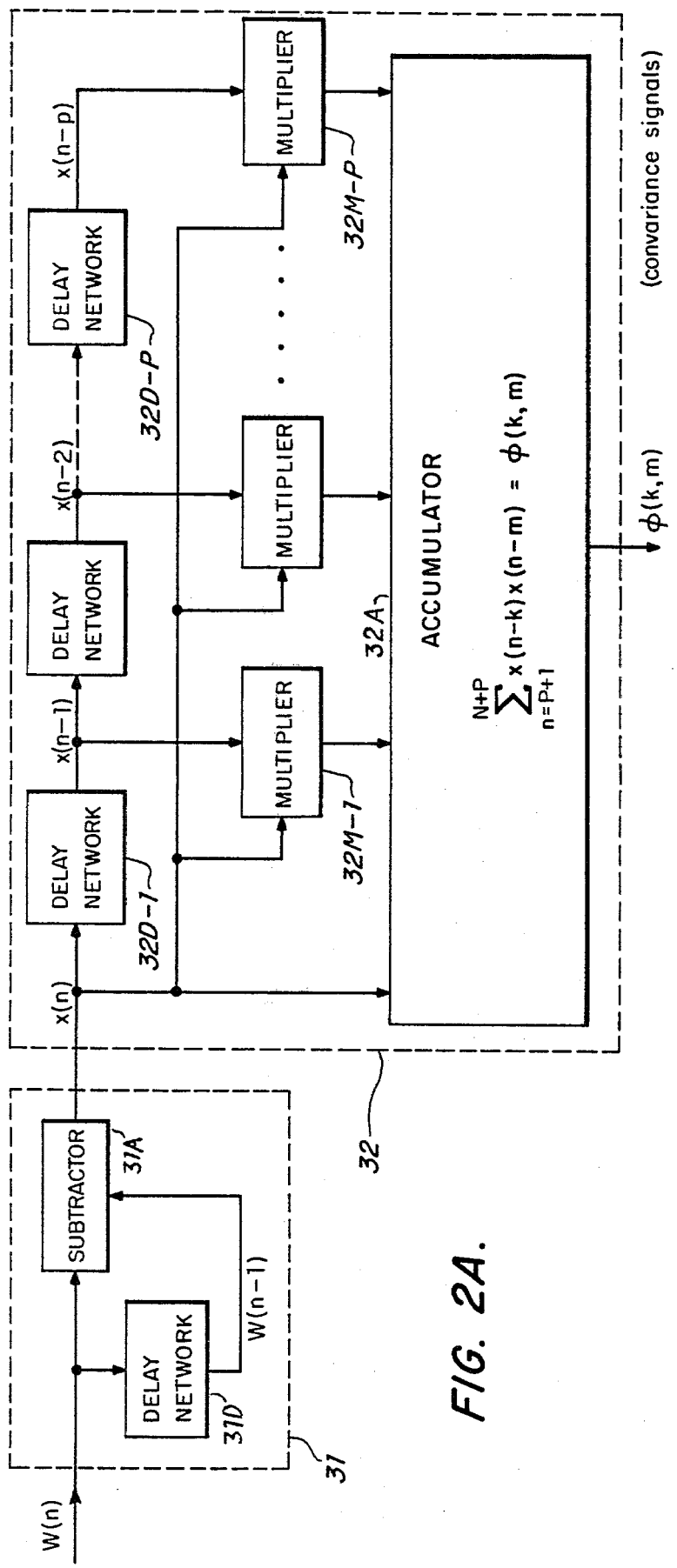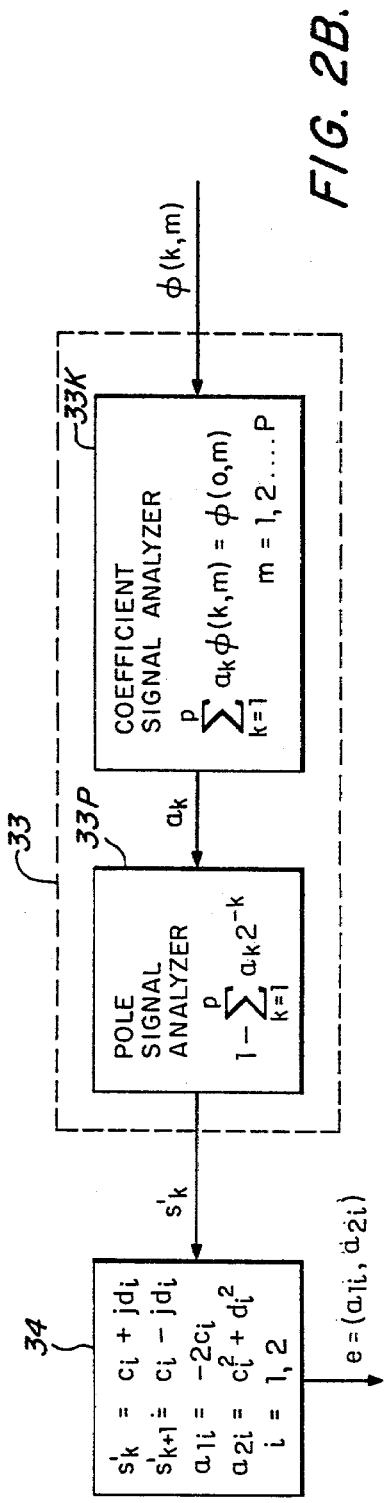
FIG. 2A.
FIG. 2B.

COMPENSATION OF FLUIDIC TRANSDUCERS

BACKGROUND OF THE INVENTION

This invention relates to fluid-filled transducers, and, more particularly, to fluid-filled transducers for making pressure measurements.

Fluid transducers are widely used in measuring physical phenomena. A typical example is the measurement of cardio-vascular pressure using fluid-filled catheters. While fluid-filled catheters do not have as desirable a frequence response as, for example, the catheter-tipped manometer, they are less fragile, less costly and less difficult to calibrate. As a result fluid-filled catheters continue to be in widespread use.

However, fluid-filled catheters produce measurements with distortions which are directly related to the physical characteristics of the catheter.

In order to provide reliable readings with fluid-filled catheters, it has been necessary to compensate for the physical characteristics of the catheter. This has been done in a variety of ways.

One technique used in compensating for the physical property of the catheter has been to use mechanical damping, as disclosed, for example, by A. C. Lapointe and F. A. Roberge in "Mechanical damping of the manometric system used in the pressure gradient technique", IEEE Transactions, Biomed. Eng. 21:76, 1974; and by R. B. Jennings Jr. and L. J. Krovets in "The use of a damping chamber and sine wave oscillator for optimal frequency response in pressure recording", In IEEE Transactions, Ind. Elec. Con. Inst. 17:134, 1970.

Another technique has been to use low pass filtering of the kind disclosed by K. L. Gould, S. Trenholmn and J. W. Kennedy in "In-vivo comparison of catheter mamometer systems with the catheter-tip mamometer", J. Appl. Physiol. 34:263, 1973, and by H. E. Dear and A. F. Spear in "Accurate method for measuring dP/dt with cardiac catheters and external transducers", J. Appl. Physio. 6:897, 1971.

Another approach has been to use analog techniques and digital techniques to provide the inverse of the catheter transfer function. Examples of the inverse analog techniques are disclosed by A. Damenstein, R. L. Stout, H. U. Wessel and H. M. Paul in "Electronic compensator for pressure waveform distortion by fluid-filled catheters", Med. & Biol. Eng., March 1978; by J. Melbin and M. Spohr in "Evaluation and correction of manometer systems with two degrees of freedom", J. Appl. Physiol., No. 5, November 1969; and H. L. Falsetti, R. E. Mates, R. J. Carroll, R. L. Gupta and A. C. Bell in "Analysis and correction of pressure wave distortion in fluid-filled catheter systems", Circulation, Vol. XLIX, January 1974.

The inverse-digital technique has been disclosed by L. J. Krovets, R. B. Jennings and S. D. Goldbloom in "Limitation of correction of frequency dependent artefact in pressure recordings using harmonic analysis", Circulation, Vol. 50, November 1974, and by S. Cicolella, L. Most, L. Jackson and D. Jaron in "Compensation of Fluid-Filled Catheter Response using Digital Filter Techniques" in PROC 4th N.E. Bioengineering Conference (May, 1976), New Haven, Connecticut.

All of the foregoing techniques have several major drawbacks. They all require pre-calibration before the instrument is placed in use. This calibration is difficult to perform in a clinical setting and the catheter response is frequently different when it is used in a patient. Consequently the compensation that is afforded by the technique, when based on a calibration that does not actually apply in a clinical situation, will be incorrect. In addition during the long term monitoring of blood pressure, for example, slow changes in the catheter response may occur. None of the foregoing compensation techniques can take into account these slow changes since they are based upon prior calibration which takes place before the instrument is placed in use, and are instead based upon a laboratory response to a test "pop" signal.

Accordingly, it is an object of the invention to facilitate the use of fluidic transducers, particularly fluid-filled catheters which are used in measuring pressure such as that exerted by the cardio-vascular system.

Another object of the invention is to compensate for the physical characteristics of fluidic transducers. A related object is to compensate for physical characteristics without the need for mechanical damping, analog low pass filtering, or the use of inverse transducer functions on an analog basis.

A further object of the invention is to avoid the need for pre-calibration of fluidic transducers in the laboratory prior to actual clinical use. A related object is to achieve compensation of fluidic transducers in the actual clinical setting.

Still another object of the invention is to avoid the need for pre-clinical calibration in clinical situations. This is to avoid the possibility that conditions in the clinical setting may be different than those of the pre-clinical calibration with the result that a prior calibration may be inappropriate to a clinical situation.

Still another object of the invention is to achieve compensation in fluidic transducers, particularly fluid-filled catheters, to compensate for long term monitoring of physical phenomena, such as blood pressure. This allows slow changes in the response of the device to be corrected without requiring any further calibration or without requiring periodic interruptions in the long term monitoring in order to check the prior calibration.

SUMMARY OF THE INVENTION

In accomplishing the foregoing and related objects, the invention provides for the monitoring of the response of a fluidic transducer and using that response to generate an error signal which controls the further filtering of the response in order to compensate for the portion of the response which is due to the transducer and not to the phenomena being measured.

In a particular embodiment of the invention applied to a fluid-filled catheter, the catheter response is applied to a predictive analyser which produces a control signal for a filter that removes the error component from the measured output, thus producing an output indication which is automatically compensated for the catheter.

In accordance with a particular aspect of the invention, the compensation is accomplished on a digital basis, with the catheter output being sampled periodically and applied both to a temporary memory taking the form of a digital store, and to a predictive digital analyser. The output of the analyser is used to control an inverse catheter digital filter to which the output of the digital store is applied. Consequently the output of the inverse catheter digital filter is the desired, compensated pressure signal which can then be used to give an accurate indication of the true state of the phenomena, for example, blood pressure of a cardio-vascular patient, being monitored by the catheter.

In accordance with another aspect of the invention, the predictive analyser includes a covariance matrix generator that acts upon a predictive analyser and a transducer parameter analyser to provide suitable filter control signals for the inverse catheter digital filter.

DESCRIPTION OF THE DRAWINGS

Other aspects of the invention will become apparent after considering several illustrative embodiments, taken in conjunction with the drawings in which:

FIG. 2A is a block diagram showing constituents for the prefilter and the covariant matrix generator in the predictive analyser of FIG. 1B;

FIG. 2B is a block diagram representation for the predictor and the filter controller of FIG. 1B;

DETAILED DESCRIPTION

Figure 1A:
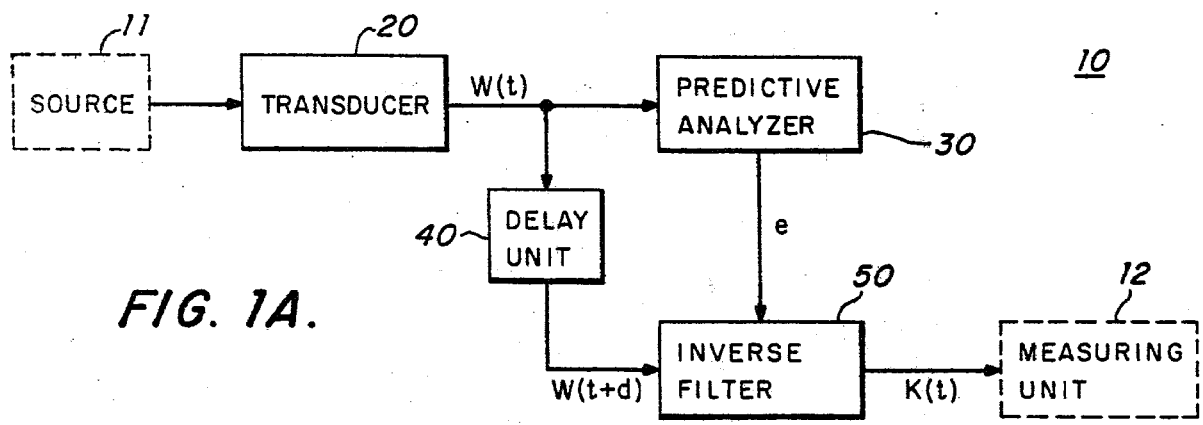
FIG. 1A is an overall block diagram of a compensation system for a fluidic transducer in accordance with the invention.

With reference to the drawings, a compensation system 10 is shown in FIG. 1A interposed between a source 11 of measurements and a measuring unit 12. The system 10 includes a transducer 20 which is connected to the source 11 in order to obtain a waveform W(t) corresponding to a physical measurement, for example, pressure, at the source 11. The waveform W(t) produced by the transducer 20 is applied jointly to a predictive analyser 30 and a delay unit 40. The purpose of the delay unit 40 is to store the signals W(t) until the predictive analyser acts upon the counterpart waveform applied to its input in order to derive an error signal e that controls an inverse filter 50 at the output of the delay unit 40. The inverse filter 50 produces a corrected output wave K(t) that is in turn applied to a measuring unit 12 where the corrected response of the measured condition is indicated, for example, by an oscilliscope or other suitable display.

The delay unit 40 desirably takes the form of a temporary memory as explained below. By acting upon the waveform W(t) the predictive analyser is able to indicate the kind of correction that is required in the waveform W(t) in order to compensate for the physical characteristics of the transducer. Accordingly, the filter 50 is of the inverse type since its input is a signal to be corrected and its output is the corrected signal.

Figure 1B:
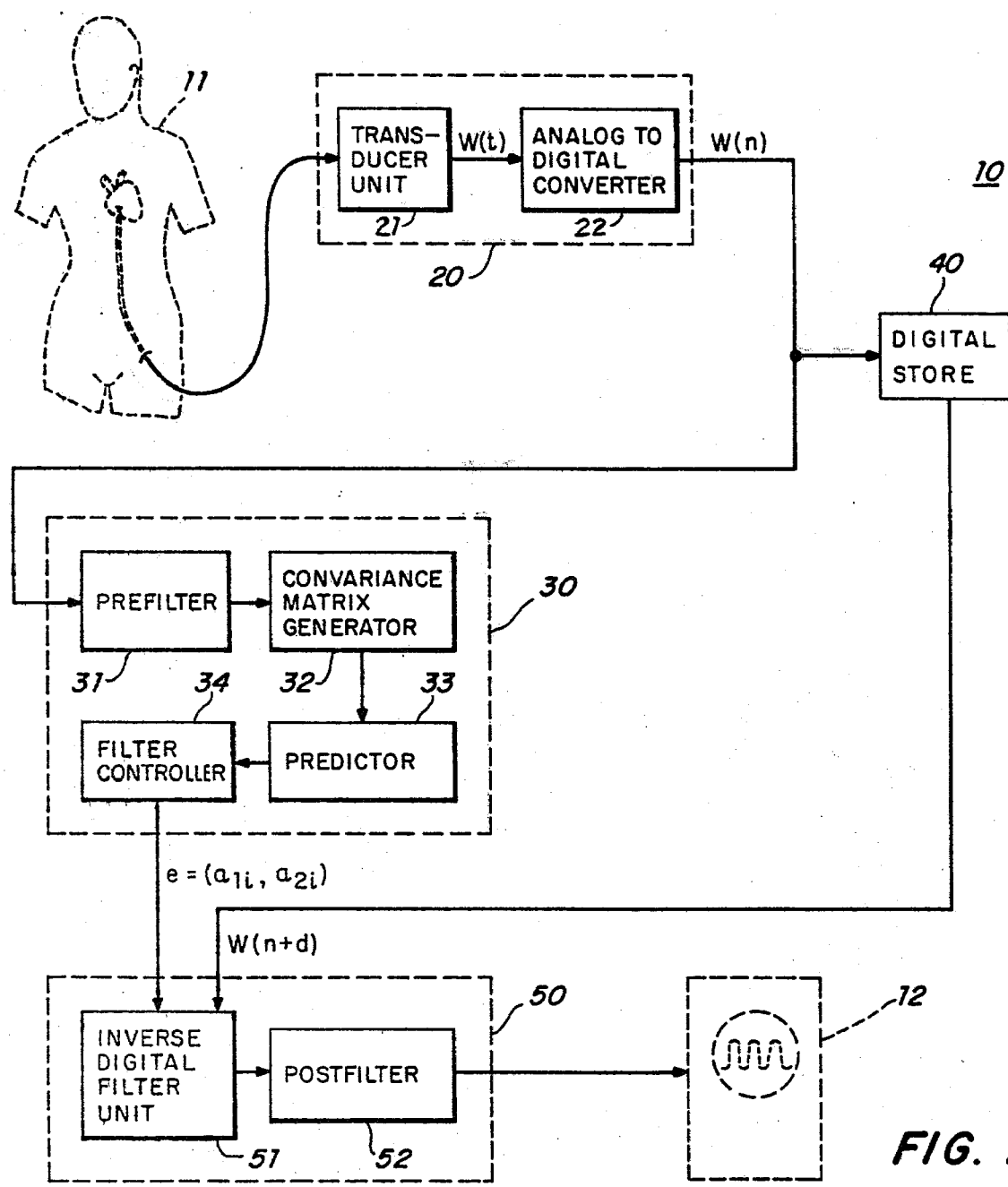
FIG. 1B is a particular adaptation of the block diagram of FIG. 1A for a fluidic catheter compensation system operating with digital signals.

The system 10 of FIG. 1A is particularly suitable for use with transducers such as fluid-filled catheters. A particular transducer for a fluid-filled cathether unit 21 is shown in FIG. 1B connected to a patient in conventional fashion in order to monitor, for example, cardiovascular pressure. In the particular implementation of the correction network 10 shown in FIG. 1B, the correction is effected on a digital basis. Consequently the transducer 20 includes an analog to digital converter 22 of customary construction. The unit 22 converts a continuously varying analog waveform W(t) into a data sequence which represents a sample pressure signal that is to be corrected. The sample signal is designated W(n), where n is an integer series ranging from one through P+N, with P referring to the order of the correction (as described below) and N referring to the number of samples in each data sequence for correction.

Samples W(n) are applied to a delay unit 40 taking the particular form of a digital store or memory. The samples are also applied to a pre-filter 31 within the predictive analyser 30. The pre-filter serves only to flatten the signal spectrum as described below. The output of the pre-filter is in turn applied to a covariance matrix generator 32 which produces covariant signals in the form of a summation of products of the various samples applied to the generator. From the covariance matrix generator the covariant signals are acted upon by a predictor 33. This produces signals that correspond to "poles" of the overall transducer. The pole signals that apply to the catheter alone, and consequently responsible for errors in response, are selectively available at the output of the predictor and are used to control the inverse digital filter by the filter controller 34.

In addition to an inverse filter unit 51, the inverse filter 50 also includes a post filter 52 which attenuates high frequency noise.

Details of the pre-filter 31 and the covariance matrix generator 32 are shown in FIG. 2A. The pre-filter 31 is formed by a delay unit 31D and a subtractor amplifier 31A. The output of the pre-filter is a signal X(n) which is applied to a delay unit chain of the covariance matrix generator 32. The delay chain includes delay units 32D-1 through 32D-P. The value p depends upon and is governed by the number of poles assigned to the transducer. These "poles" represent the natural frequencies of the waveform applicable to the phenomena, and to the error caused by the physical characteristics of the transducer. It is the latter that are to be compensated by the system.

In order to arrive at the covariance signals, each delayed signal and the undelayed signal are multiplied by the undelayed signal, in accordance with the equation (1) below:

$$\phi(k,m) = \sum_{n=P+1}^{N+P} x(n-k)x(n-m) \tag{1}$$

where m is equal to 1,2, ... P and k is equal to 0,1 ... P.

The covariance matrix generator therefore includes P+1 multiplier units which are designated 32M-0 through 32M-P. As noted below P is desirably four or six.

The multiplier outputs are applied to an accumulator 32A in order to derive the covariance output signals $\phi(k,m)$ of equation (1). The accumulation functioning takes place in standard fashion to achieve the result of equation (1).

The covariance signals from the accumulator 32A are applied to a predictor 33 shown in FIG. 2B. The first unit of the predictor 33 is a coefficient signal analyser 33K which produces coefficient signals $a_k$ by implementing in standard fashion equation (2) set forth below:

$$\phi(0,m) = \sum_{k=1}^{P} a_k \phi(k,m) \tag{2}$$

where m is as in equation (1) above.

The coefficient signals $a_k$ from the analyser 33K are applied to a pole signal analyser 33P and manipulated to derive pole signals $s'_k$. The desired pole signals $s'_k$ are produced in standard fashion by evaluating the variable z of equation (3).

$$H(z) = 1 - \sum_{k=1}^{P} a_k z^{-k} = 0 \qquad (3)$$

where $H(z)$ is a system function and the variable z when evaluated provides the "zeros" of the system function.

Some of the zeros of the system function $H(z)$ correspond to poles of the pressure waveform and the remaining zeros correspond to poles of the catheter. It is the poles of the catheter that are removed by the inverse filter 50 to derive the corrected pressure waveform.

Figure 4A:
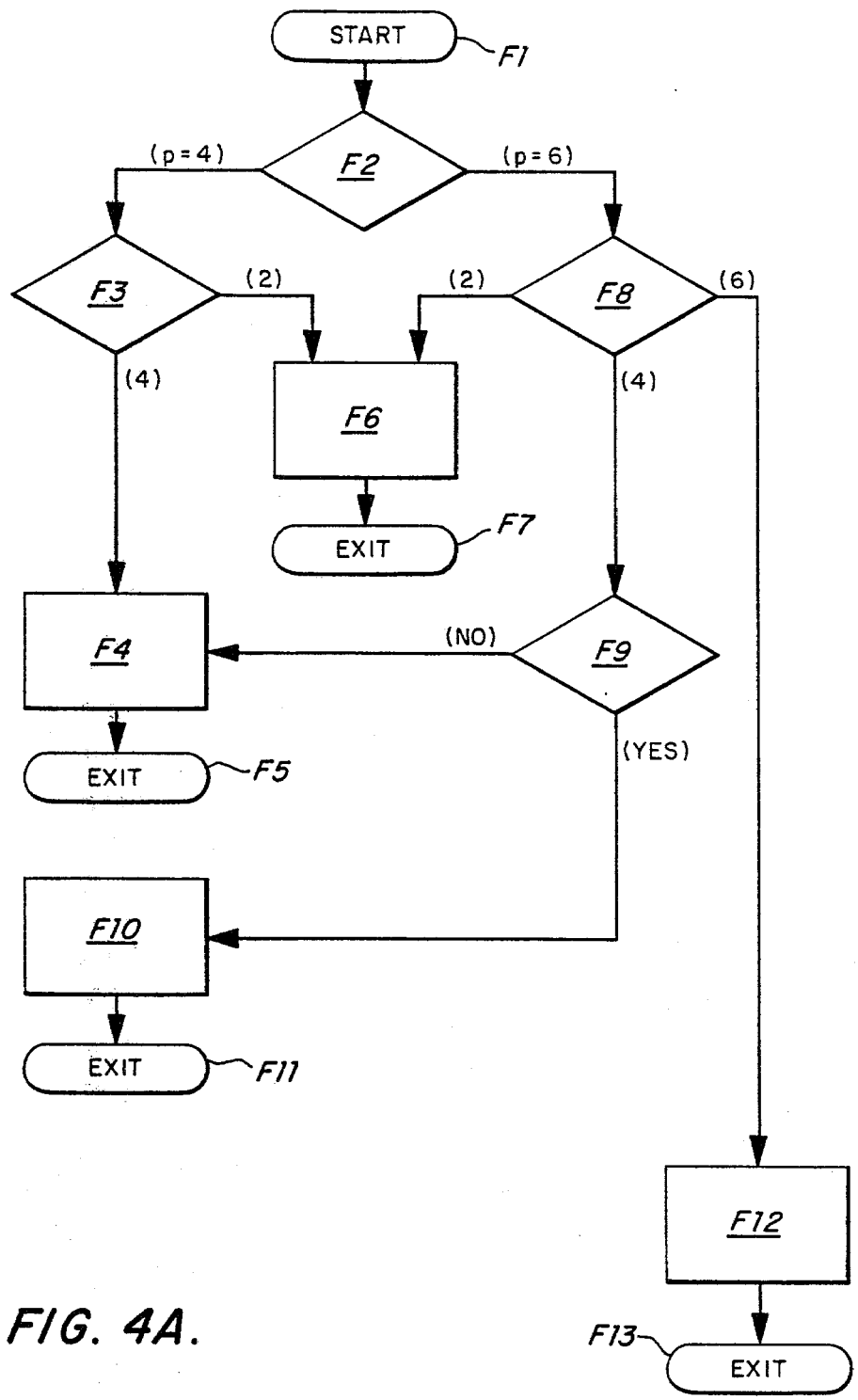
FIG. 4A is a flow chart for selecting the compensation parameters which act upon the filter controller of FIG. 1B.
Figure 4B:
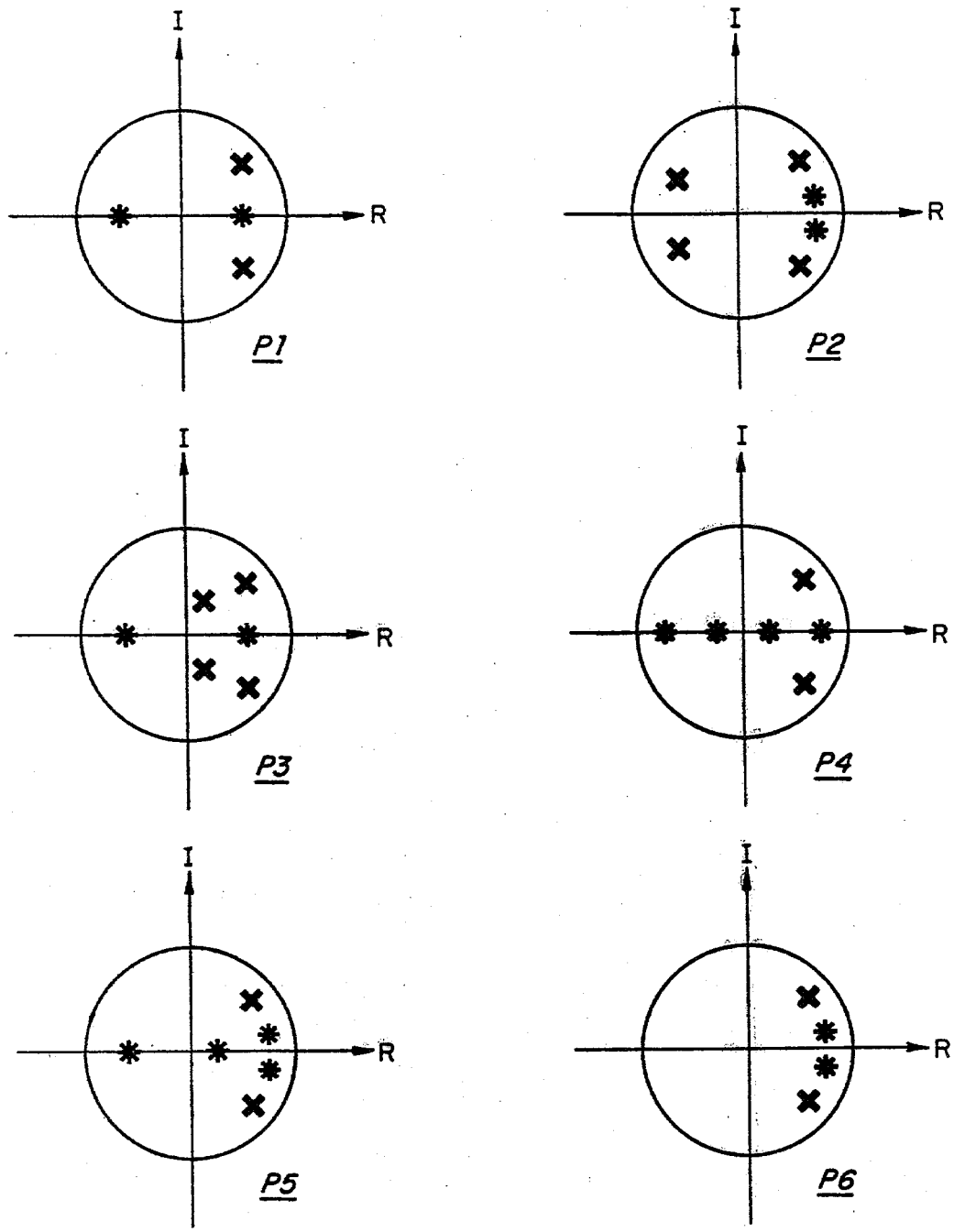
FIG. 4B is a pole plot which is applicable to the compensation system of FIG. 1A and the flow chart of FIG. 4A.

The pole signals $s_k$ are sorted to include only those pole signals $s'_k$ which are attributable to the catheter. This sorting process can be accomplished in a wide variety of ways and a programming technique for doing so is discussed below. Illustrative pole signal plots $P_1$ through $P_6$ are set forth in FIG. 4B. Each pole plot includes poles associated with the catheter, designated by X's and pole signals associated with pressure waveforms designated by asterisks. Each pole plot has a real axis R and a quadrature axis I. To the extent that a pole is removed in angle from the positive real axis R it represents an oscilliatory behavior. To the extent that a pole is removed from the unit magnitude circle it represents a damped signal response. It has been determined experimentally that the catheter pole signals are those which show the greatest oscilliatory response and least damping as is evident from the various plots of FIG. 4B. Consequently, the desired pole signals can be sorted in the pole signal analyser 33 by standard fashion so that only the sorted pole signals $s'_k$ are applied to the filter controller 34 of FIG. 2B. The catheter pole signals can be represented as shown in equation (4) below:

$$s_k' = c_i + jd_i \qquad (4)$$

$$s'_{k+1} = c_i - jd_i$$

where c corresponds to the real portion of the signal along the real axis R of the pole plot such as that of FIG. 4B, d corresponds to the quadrature component along the quadrature axis I of FIG. 4B, and j indicates that the d signal component is in quadrature.

The filter controller 34 combines the various signal components of equation (4), in standard fashion, to produce the filter controller signals $a_{1i}$, $a_{2i}$ of equation (5).

$$a_{1i} = -2c_i \text{ and} \qquad (5)$$

$$a_{2i} = c_i^2 + d_i^2$$

where i equals 1,2.

Figure 3:
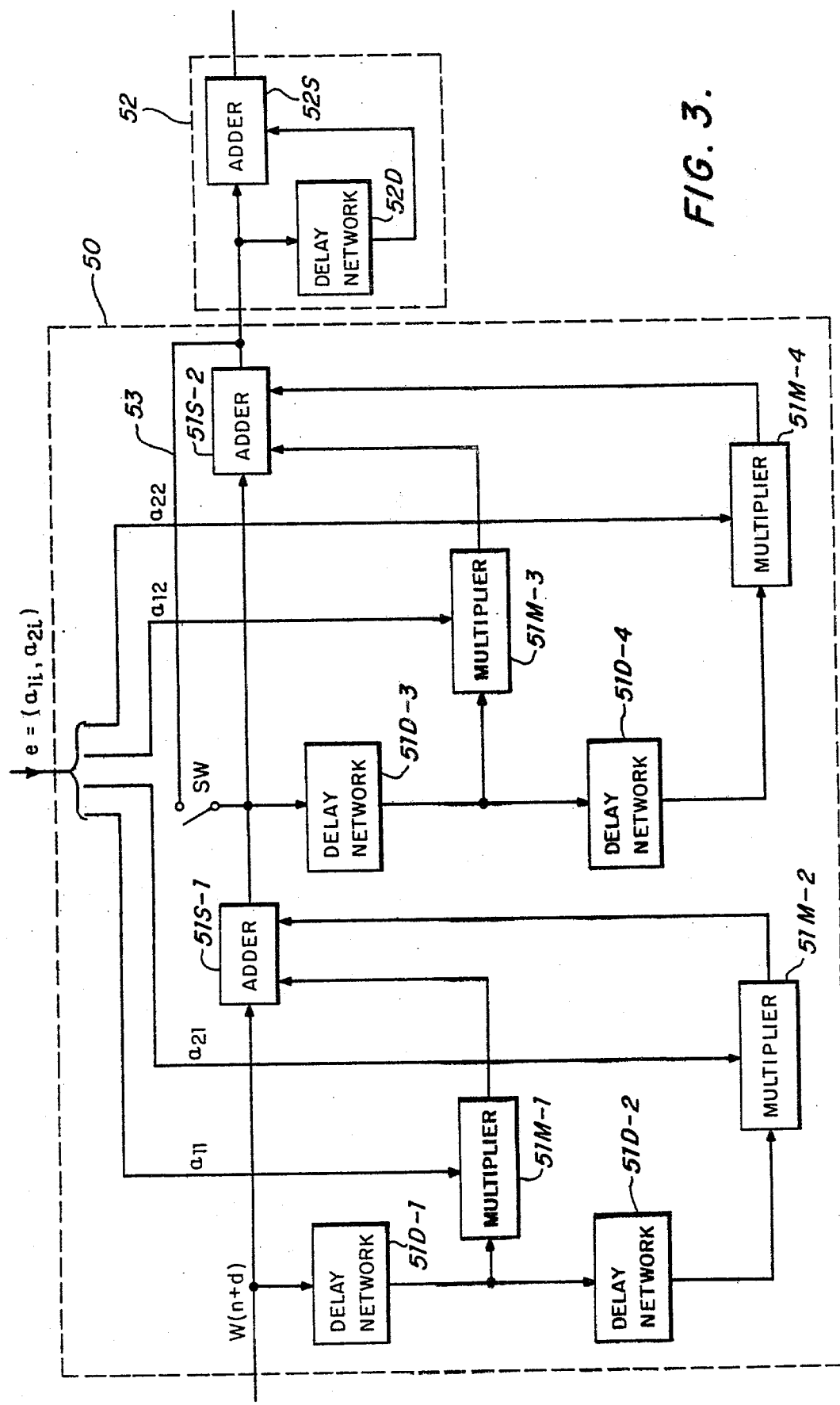
FIG. 3 is a block diagram of the inverse digital filter for the network of FIG. 1B.

The signal levels $a_{1i}$ and $a_{2i}$, where i is 1 or 2, control multiplier boxes in FIG. 3 as indicated. In particular, the waveform W(n+d) which is derived from the digital store 40 is applied to a unit delay network 51D-1 and then to a second delay network 51D-2. After passing through delay unit 51D-1 the signal is then applied to a first multiplier network 51M-1 and multiplied by the filter signal $a_{11}$. The output of the second delay unit 51D-2 is applied to a second multiplier unit 51M-2 where it is multiplied by the filter signal $a_{21}$. The multiplied signals are added in a summing network 51S-1. If there are only two poles to be compensated, the output of the adder 51S-1 is applied, after closure of a switch SW, over a shunt 53 to a post filter 52.

However, if there are four catheter poles which are to be compensated, the output of the first summing network 51S-1 is applied to a third delay unit 51D-3 and in turn to a third multiplier 51M-3 where the delay output is multiplied by the filter signal $a_{12}$. In addition a fourth delay unit 51D-4 has its output applied to a fourth multiplier 51M-4 where it is multiplied by the signal filter $a_{22}$. The summation is then produced at a second summing network 51S-2 and then applied to the post filter 52.

In effect the system function $H_F(z)$ of the inverse filter 50 is as stated in equation (6).

$$\prod_{k=1}^{K} (1 - s_k' z^{-1}) = \prod_{i=1}^{2} (1 + a_{1i} z^{-1} + a_{2i} z^{-2}) \qquad (6)$$

As noted above, it is possible to implement the selection of the poles for which compensation is to be undertaken using the flow chart of FIG. 4A in either hardware or software terms. After starting (block F1), a selection is made according to whether the waveform has six poles or four poles, i.e., P=4 or P=6, by the decisional block F2. If the response has four poles a second decision is made in block F3 as to whether there are two or four complex conjugate poles.

If there are two complex conjugate poles as indicated by block F6, they are used to produce the filter control signals and the program is terminated (block F7). However, if there are four complex conjugate poles, the two poles with the largest magnitude and natural frequency are selected by block F4 and the program is terminated. The alternative decision made at the decisional block F2 is that the number of poles is equal to six, in which case a sorting is made in block F8 between the two, four or six poles to determine how many are complex conjugate. If two of the poles are complex conjugate, they are selected by block F6 for which compensation is undertaken and the procedure is ended. If all four poles are appropriate as catheter poles, as determined by block F9, then blocks F10 and F11 end the program. However, if they are not, the two poles with the largest magnitude, following the same procedure as for four poles is determined in block F4. The remaining case is where there are six complex conjugate poles, in which case block F9 excludes the two that are most likely associated with the pressure signal itself, i.e., those having the lowest natural frequencies as indicated in FIG. 4B.

While various aspects of the invention have been set forth by the drawings and specification, it is to be understood that the foregoing detailed description is for illustration only and that various changes in parts, as well as the substitution of equivalent constituents for those shown and described may be made without departing from the spirit and scope of the invention as set forth in the appended claims.

What is claimed is:

1. The method of compensating digitized pressure waveform output indicators of a fluid-filled catheter transducer which comprises the steps of:

(a) generating from the digitized pressure waveform output indications pole signals that are associated with the fluid-filled catheter; and, (b) inverse filtering the digitized pressure waveform output indications under the control of said pole signals to cancel said pole signals.

2. The method of claim 1 wherein the digitized pressure waveform is stored in a digital memory before being filtered.

3. The method of claim 1 wherein the generating step includes the generation of covarient signals from the digitized waveform, the generation of coefficient signals from said covarient signals, and the generation of said pole signals from said coefficient signals.

4. The method of claim 1 wherein the filter control signals are generated from selected ones of said pole signals.

5. The method of claim 4 wherein said pole signals are selected from those having the largest natural frequency components.

6. The method of claim 5 wherein the selected pole signals are those with the least damping.

7. The method of claim 4 wherein the number of pole signals is either two or four.

8. Apparatus for compensating digitized pressure waveform output indications of a fluid-filled catheter transducer which comprises:

means for generating from said digitized pressure waveform output indications pole signals associated with the fluid-filled catheter; and, means for inverse filtering the digitized pressure waveform output indications under the control of said pole signals to cancel said pole signals.

* * * * *